(12) United States Patent
Min (10) Patent No.: US 8,192,386 B2
(45) Date of Patent: Jun. 5, 2012

(54) SYSTEM AND METHOD FOR CONTROLLING HEMATOCRIT DURING A THERAPEUTIC RED BLOOD CELL EXCHANGE PROCEDURE

(75) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 382 days.

(21) Appl. No.: 12/392,239

(22) Filed: Feb. 25, 2009

(65) Prior Publication Data

US 2009/0211987 A1 Aug. 27, 2009

Related U.S. Application Data

(60) Provisional application No. 61/031,727, filed on Feb. 27, 2008.

(51) Int. Cl.
*A61M 37/00* (2006.01)
*C02F 1/44* (2006.01)
(52) U.S. Cl. ............... 604/6.02; 604/6.01; 604/6.04; 604/6.1; 210/645
(58) Field of Classification Search .............. 604/4.01, 604/5.01, 6.01, 6.02, 6.04, 6.11, 6.16; 210/645, 210/513, 516
See application file for complete search history.

(56) References Cited

U.S. PATENT DOCUMENTS

| | | | | |
|---|---|---|---|---|
| 5,141,645 | A | * | 8/1992 | Shiraki et al. ............ 210/513 |
| 6,945,948 | B2 | * | 9/2005 | Bainbridge et al. ...... 604/6.04 |
| 7,282,154 | B2 | | 10/2007 | Muller |

* cited by examiner

*Primary Examiner* — Leslie Deak
(74) *Attorney, Agent, or Firm* — Cook Alex Ltd.

(57) ABSTRACT

Systems and methods for controlling hematocrit during a blood processing procedure. In one aspect, a system includes a first flow path for flowing whole blood from a patient. A separator communicates with the first flow path for separating at least red blood cells from plasma. Second and third flow paths communicate with the separator for respectively flowing the separated plasma and red blood cells from the separator. A flow controller is associated with the second and third flow paths to control fluid communication between the second and third flow paths and addition of separated plasma to the separated red blood cells. The resulting red blood cells and plasma has a resulting hematocrit. Hematocrit is calculated or sensed in operative association with the third flow path and communicated to the flow controller for controlling the amount of plasma added to the third flow path and the resulting hematocrit.

16 Claims, 4 Drawing Sheets

SYSTEM AND METHOD FOR CONTROLLING HEMATOCRIT DURING A THERAPEUTIC RED BLOOD CELL EXCHANGE PROCEDURE

CROSS-REFERENCE TO RELATED APPLICATION

This application claims the benefit of U.S. Provisional Patent Application Ser. No. 61/031,727, filed on Feb. 27, 2008, the disclosure of which is hereby incorporated herein by reference.

BACKGROUND

This disclosure generally relates to a biological fluid processing system and method thereof. More specifically, this disclosure relates to a system and method for a therapeutic exchange procedure that exchanges at least one constituent component, such as a blood component, from a withdrawn biological fluid, such as whole blood, from a patient with one or more replacement fluids that are infused to the patient.

Blood processing systems and methods that relate to a therapeutic exchange procedure typically withdraw a biological fluid, such as whole blood, from a patient. The biological fluid, such as whole blood, may be directed to a separator, such as a centrifugal or membrane assembly, for separation of at least one constituent component, such as at least one blood component, for example, red blood cells, plasma and/or platelets, from the remaining blood components. Depending on the procedure, certain separated constituent components may be retained by the system and not returned to the patient. The remaining separated constituent components may be returned to the patient together with one or more fluids to replace the constituent retained by the system. The particular separated constituent that is not returned to the donor may depend on the specific medical needs of the patient. For example, one type of therapeutic exchange procedure is a red blood cell exchange procedure that removes a quantity of separated red blood cells from the withdrawn whole blood of a patient and returns to the patient at least one replacement fluid, such as fresh red blood cells from a healthy donor, an additive solution or other fluid, along with the remaining separated blood components.

In a therapeutic exchange procedure, it is generally desired to maintain a patient's fluid balance such that the difference between the amount of removed fluid and replaced fluid is within a desired range. However, in a red blood cell exchange procedure it may also be desired to monitor the hematocrit of the removed red blood cells so as to avoid the patient receiving too many or too few replacement red blood cells. For example, during a red blood cell exchange procedure, if the removed red blood cells have a hematocrit that is higher than the replaced red blood cells then the patient receives too few red blood cells. If the removed red blood cells have a lower hematocrit than the replaced red blood cells, then the patient receives too many red blood cells.

SUMMARY

In one aspect, the present disclosure is directed to a system for controlling hematocrit during a blood processing procedure. The system may include a first flow path for flowing whole blood from a patient. A separator may communicate with the first flow path for separating at least red blood cells from the blood. The system may further include a second flow path that communicates with the separator for flowing the separated components, such as plasma, from the separator and a third flow path that communicates with the separator for flowing the separated red blood cells from the separator. The system further may include a flow controller associated with the second and third flow paths to control fluid communication between the second and third flow paths and to control addition of separated plasma to the separated red blood cells. The resulting combined red blood cells and plasma has a resulting hematocrit. (Hematocrit is the measure of the fluid volume that is made up of red cells. For example, if red cells make up 40% of the volume of the combined fluid, the resulting hematocrit is "40"). A hematocrit sensor may be operatively associated with the third flow path to determine the hematocrit therein, or this may be calculated by the controller based on selected parameters. The sensor preferably communicates with the flow controller, or the flow controller utilizes the calculated hematocrit in the third flow path, for controlling the amount of plasma added to the third flow path and the resulting hematocrit. The system may be particularly useful where the flow controller includes a programmable controller that may be programmed to control the resulting hematocrit at about a desired level. Such resulting hematocrit may be selectable to be substantially the same as a known hematocrit of replacement red blood cells so that the amount of red cells removed is approximately equal to the amount of red cells added. The flow controller may further be adapted to alternate the flow of separated plasma between flow to the third flow path and return flow to the patient, such as by employing a valve or similar structure.

In another aspect, a system for controlling hematocrit during a blood processing procedure includes a replacement fluid flow path that communicates with replacement red blood cells from a source of replacement red blood cells having a known hematocrit. The system also may include a first flow path for flowing whole blood from a patient to a separator for separating the whole blood into at least red blood cells from plasma. The system may further include a second flow path that communicates with the separator for flowing plasma separated from the patient's blood out of the separator and a third flow path that communicates with the separator for flowing the separated red blood cells (from the patient's blood) from the separator. A controller may be associated with the second and third flow paths to control fluid communication between the second and third flow paths so as to control addition of separated plasma to the separated red blood cells. The resulting red blood cells and plasma preferably has a resulting hematocrit. A hematocrit sensor may be operatively associated with the third flow path to determine the hematocrit therein and to communicate with the controller for controlling the amount of plasma added to the third flow path and the resulting hematocrit, or the controller may calculate the hematocrit in the third flow path and control the amount of plasma added to the third flow path and the resulting hematocrit. Such system may be particularly useful where the controller includes a programmable controller that may be programmed to control the resulting hematocrit at about a desired level that is substantially the same as the known hematocrit. The system may be adapted to alternate the flow of the separated plasma between flow to the third flow path and return flow to the patient, such as by employing a valve or similar structure.

In a further aspect, the present disclosure is directed to a method for controlling hematocrit during a blood processing procedure. Such a method may include withdrawing whole blood from a patient and separating the whole blood withdrawn from the patient into at least separated plasma and separated red blood cells having a hematocrit. The method may also include determining the hematocrit of the separated red blood cells. The method may further include adding separated plasma to separated red blood cells as necessary to achieve a desired resulting hematocrit. Such method may include controlling the resulting hematocrit at about a desired level, such as controlling the resulting hematocrit to be substantially the same as a known hematocrit of replacement red blood cells. Such method may include alternately returning separated plasma to the patient and adding separated plasma to the separated red blood cells.

In a yet further aspect, a method for controlling hematocrit during a blood processing procedure includes introducing replacement red blood cells of a known hematocrit into a patient. Such a method may include withdrawing whole blood from the patient and separating the whole blood withdrawn from the patient into at least separated plasma and separated red blood cells having a hematocrit. Such a method may also include sensing or calculating the hematocrit of the separated red blood cells. Further, such method may include adding separated plasma to separated red blood cells as necessary to achieve a desired resulting hematocrit that is substantially the same as the known hematocrit of the replacement red blood cells. Such method may particularly be useful in controlling the resulting hematocrit at about a desired level that is substantially the same as the known hematocrit. In yet another aspect, such method may include alternately returning separated plasma to the patient and adding separated plasma to the separated red blood cells.

DETAILED DESCRIPTION

Figure 1:
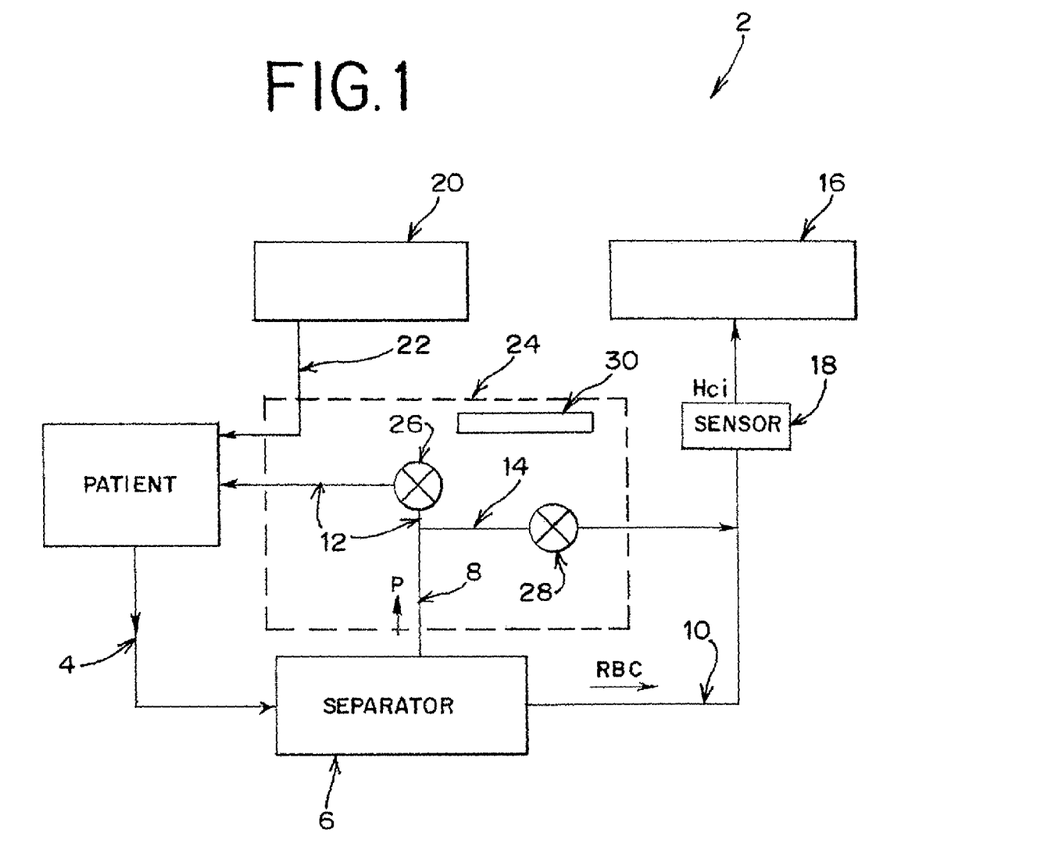
FIG. 1 a diagrammatic view of a system and method in accordance with one embodiment of the subject matter described herein.

In accordance with one embodiment of the present disclosure, FIG. 1 illustrates a processing system, generally indicated at 2, that may be used for processing various fluids in accordance with the subject matter described herein. The system 2 is particularly well suited to processing whole blood and/or other suspensions of biological fluids. Although the processing of whole blood will be described, the illustrated embodiments are not limited to such processing and may be employed for processing other biological fluids. By way of example and not limitation, the systems described herein are particularly suited for a therapeutic red blood cell exchange procedure during which red blood cells are separated from withdrawn whole blood and the remaining blood components and fresh or replacement red blood cells alone or with other replacement fluid, such as an additive solution commercially sold under the trademark Adsol®, is returned to a patient. It is understood that the systems described herein are not limited to such procedure and that other procedures are also possible.

In FIG. 1, the system 2 includes a first flow path, generally indicated at 4, that communicates with a patient for flowing (withdrawing) at least a first fluid, such as whole blood, from the patient. In FIG. 1, a separator, generally indicated at 6, may be associated with the first flow path 4 for receiving the whole blood and separating the whole blood from the patient into one or more separated blood components. By way of example, the separator 6 may separate primarily red blood cells from plasma and preferably separates red bloods cells from the remaining blood components, e.g., plasma, platelets and white blood cells. In FIG. 1, a second or plasma flow path, generally indicated at 8, preferably communicates with the separator 6 for flowing the separated plasma and/or other remaining blood components, such as platelets and/or white blood cells, from the separator 6. A third or red blood cell flow path, generally indicated at 10, preferably communicates with the separator 6 for flowing the separated red blood cells from the separator.

The separated plasma may flow from the separator 6 generally in two ways or along two branches of the second flow path 8, such branches generally indicated at 12 and 14. A first branch 12 may communicate, either directly or indirectly with the patient and a second branch 14 may communicate with the red blood cell flow path 10 at a selected location to combine and/or mix with the separated red blood cells.

Also in FIG. 1, a first container or reservoir, generally indicated at 16, is preferably associated with the red blood cell flow path 10, such as at a downstream end of such flow path 10. The first reservoir 16 preferably communicates with the separator 6 to allow the separated red blood cells to flow from the separator 6 to such reservoir 16. A monitoring device, such as a sensor, generally indicated at 18, may be associated with the third flow path 10 at a sensing location that is preferably downstream of the selected location where separated plasma in flow path 14 and red blood cells in flow path 10 may combine. Alternatively, the hematocrit of the flow into reservoir 16 may be calculated based on other selected parameters, such as including the inlet hematocrit in flow path 4 and the flow rate in flow path 4, the configuration of the separator (such as in a centrifuge, the area of sedimentation, the acceleration of the centrifuge, and the sedimentation coefficient), and other characteristics of the blood (such as viscosity). These parameters may be used to determine via calculation the hematocrit as set forth in the article entitled The Physics of Continuous Flow Centrifugal Cell Separation, by Brown, Richard I., Artificial Organs, 1989, Vol. 13, No. 1, at pages 4-20, incorporated by reference herein. This, together with the plasma added to the flow from flow path 10 results in the hematocrit of the flow into reservoir 16. In FIG. 1, a second reservoir, generally indicated at 20, may be associated with a source of a replacement fluid, such as fresh red blood cells, and may communicate with the patient, either directly or indirectly, by way of a replacement fluid flow path, generally indicated at 22. Although in FIG. 1, the replacement red blood cells flow to the patient separately from the separated plasma, it is also possible for the replacement red blood cells and separated plasma to flow by way of a combined flow path that communicates either directly or indirectly with the patient.

In FIG. 1, a controller or flow controller, generally indicated at 24, may be associated with one or more flow controlling devices, such as, for example, valves, generally indicated at 26 and 28, that preferably control the addition of the separated plasma to the separated red blood cells. In FIG. 1, such valves 26 and 28 are preferably respectively associated with the first and second branches 12 and 14 of the plasma flow path 8 for respectively controlling fluid flow of the separated plasma either to the patient or to the plasma flow path 10. By way of example, when the valve 26 is open and the valve 28 is closed, the separated plasma is directed to the patient. Alternatively, when the valve 26 is closed and the valve 28 is opened, the separated plasma is directed to the separated red blood cells in the red blood cells flow path 10. Other types of flow controlling devices may also be used as controllers, including but not limited to pumps, such as peristaltic or diaphragm pumps, as well as gravity-controlled flow controllers. The controller 24 may also be associated with the replacement fluid flow path 22 for controlling the fluid flow of the replacement fluid and may include various pumps, valves or other similar structures for controlling such flow.

In FIG. 1, such controller 24 may include a main controller, generally indicated at 30, such as a programmable controller employing a programmable microprocessor, that is operatively associated with the first and second valves 26 and 28 to control the fluid flow through each valve. The controller 30 may also be operable to determine and/or control the respective flow rates of the separated plasma, separated red blood cells and/or the replacement fluid, such as described in copending U.S. Patent Application Ser. No. 61/031,724, entitled "System And Method For Controlling Patient Fluid Balance And/Or Flow Rate For A Therapeutic Plasma Exchange Procedure", filed on Feb. 27, 2008, and hereby incorporated by reference.

Figure 2:
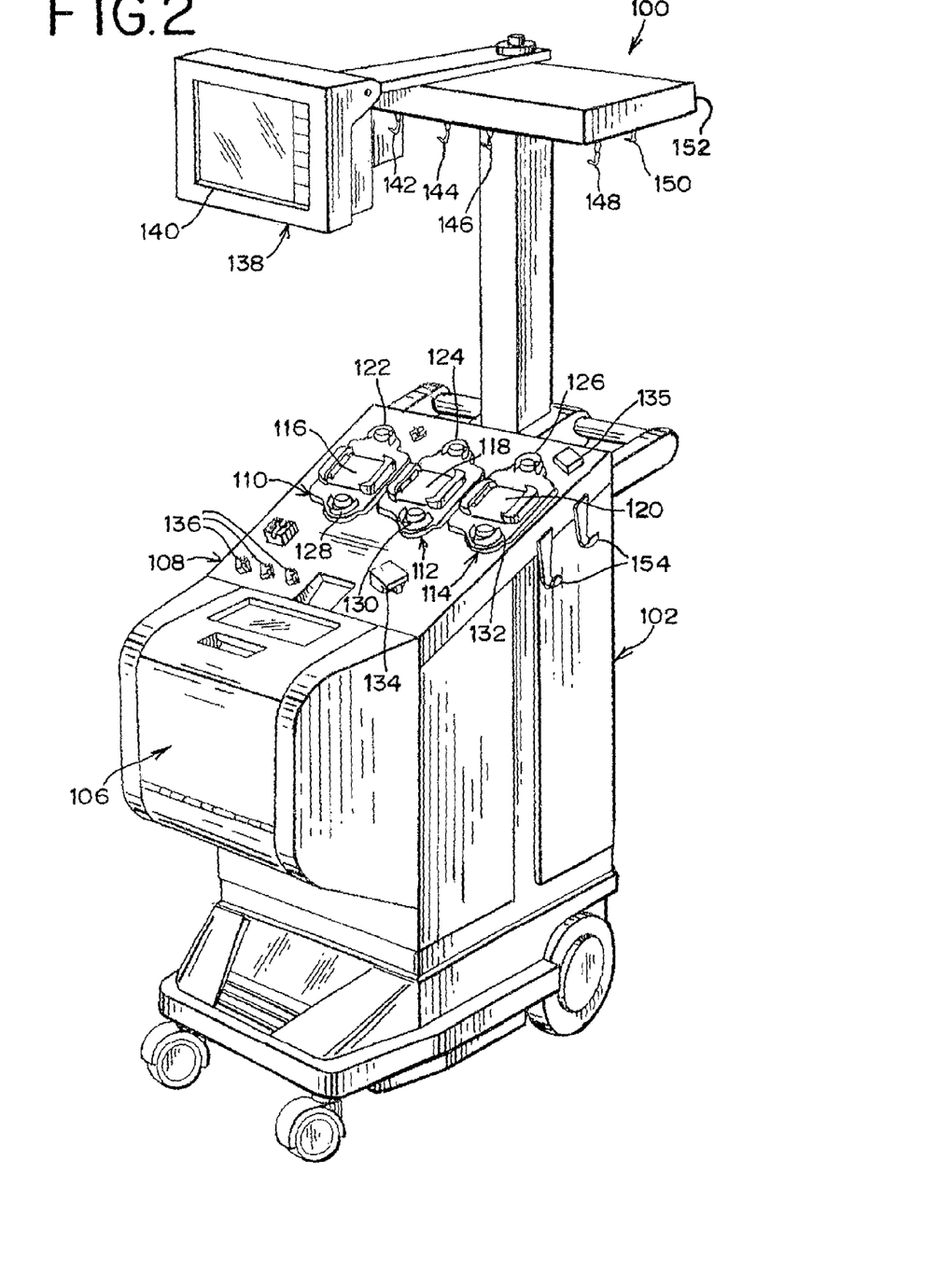
FIG. 2 is a perspective view of a reusable blood processing device that may be employed as part of or in association with the subject matter described.

In accordance with another embodiment, FIG. 2 illustrates a centrifugal processing device, generally indicated at 100, that can be used for processing various fluids. The illustrated embodiment is substantially identical to a commercial centrifuge sold by Fenwal, Inc. as the Amicus® separator, which is disclosed in numerous patents and patent applications, not limited to but including U.S. Pat. No. 5,868,696, to Giesler et al., issued Feb. 9, 1999, which is incorporated herein by reference. It is understood that the present disclosure is not limited to such a device or to the processing of whole blood, and that the present disclosure may have application in a variety of settings where processing of biological fluid is desired.

Figure 3:
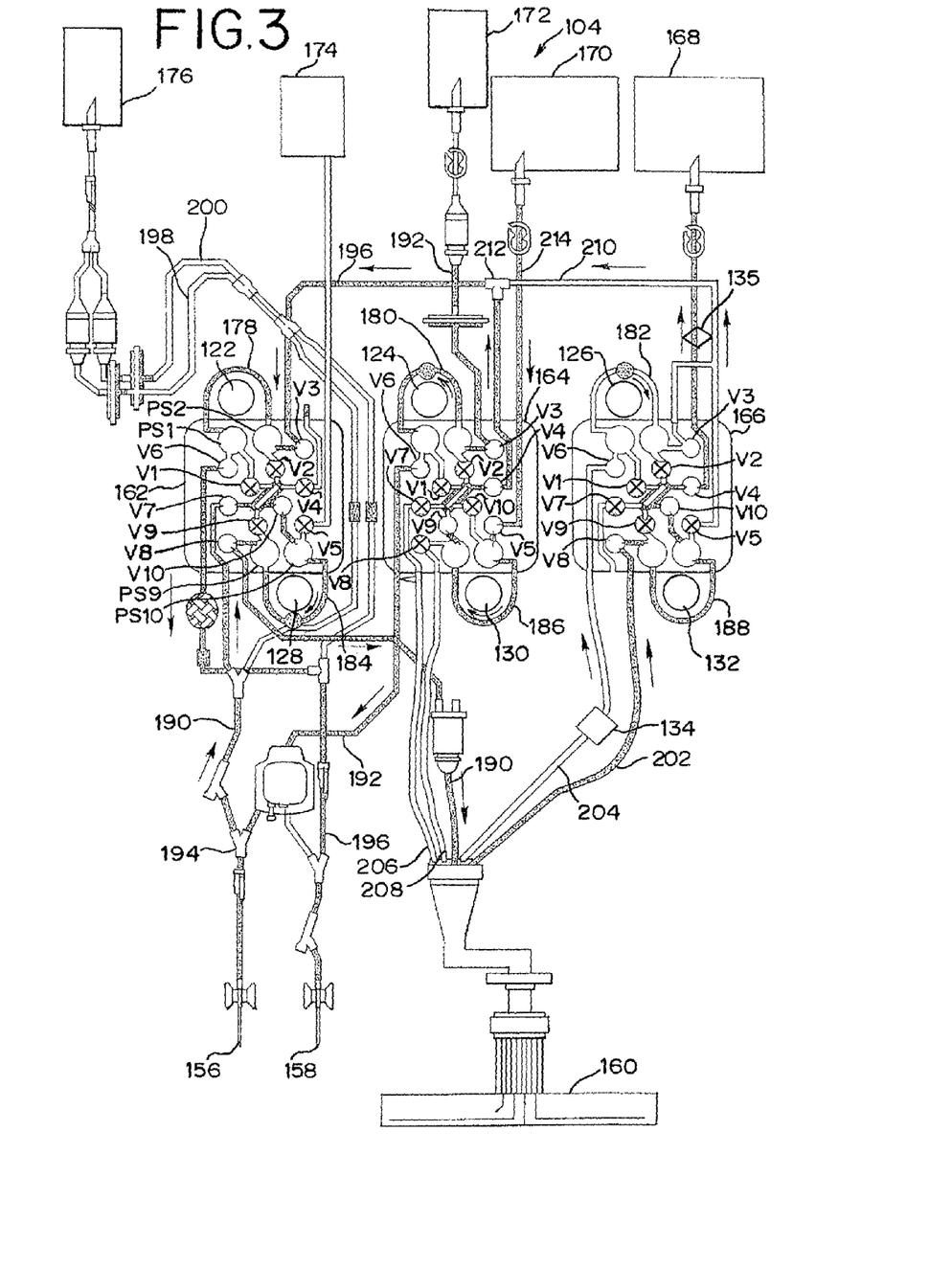
FIG. 3 is a plan view of a disposable tubing flow set for use with the processing device shown in FIG. 2, illustrating flow through the set.
Figure 4:
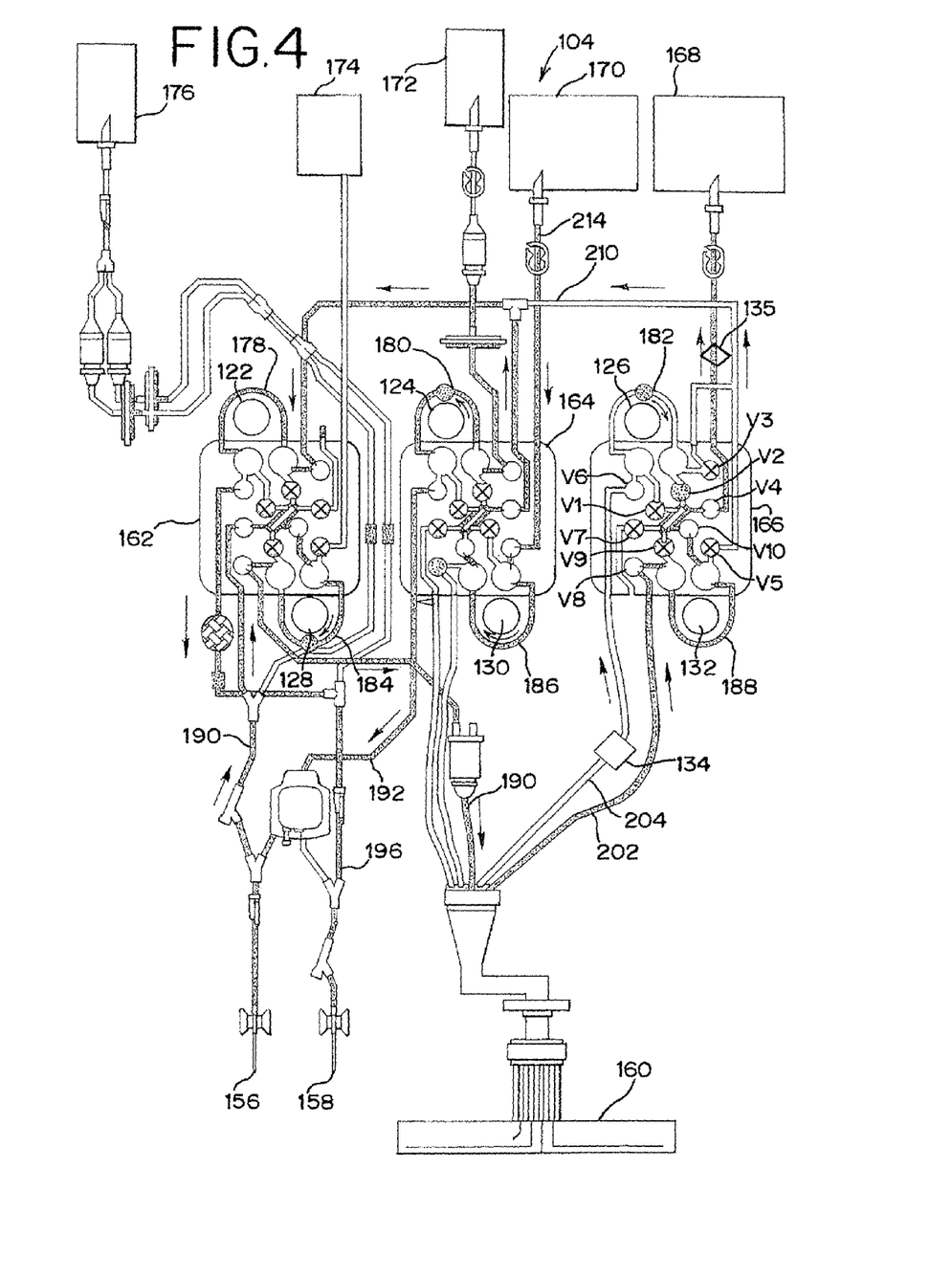
FIG. 4 is a plan view of a disposable set, similar to FIG. 3, showing an alternate flow pattern.

In FIG. 2, the centrifugal processing device 100 includes a separation assembly, specifically a centrifuge rotor assembly, generally within the housing indicated at 102, and is configured to control fluid flow through a disposable fluid processing set in FIGS. 3-4, generally indicated 104, used in association with the processing device 100. As noted above, the separation assembly need not be a centrifugal processing assembly, such as that disclosed and shown in U.S. Pat. No. 5,868,696, and other separation technology or devices, such as membrane separators, may also be used. The separation assembly 102 receives and separates a biological fluid, such as whole blood and/or other biological fluids, into two or more constituent components. The separation assembly 102 is preferably adapted to be durable and reusable over a long term. The fluid processing set 104, in contrast, is preferably disposable and a fresh sterile set may be assembled with the separation assembly 102 for each use.

In FIG. 2, the separation assembly 102 includes an access compartment, generally indicated at 106, which houses a portion of the disposable set 104, such that when the separation assembly 102 is activated, the constituent components are separated within such portion of the set 104. A panel, generally indicated at 108, provides a surface for receiving another portion of the disposable set 104. For example, the panel 108 includes three pumping and valving stations, or respective left, middle and right stations, generally indicated at 110, 112 and 114, in FIG. 2, and each station 110, 112 and 114 respectively includes a valve interface portion 116, 118 and 120, that controls the opening and closing of associated valves in a disposable flow control cassette, described further below. Each station also has a respective upper flow controlling device or pump 122, 124, 126 and a lower flow controlling device or pump 128, 130, 132. Each illustrated pump 122, 124, 126, 128, 130, 132 is a peristaltic pump adapted to be associated with a section of tubing to provide flow control, although other types of pumps or other flow controlling devices, such as diaphragm pumps or gravity controlled devices are also possible. The panel 108 may further include a detector 134, such as an optical detector, a hematocrit sensor 135 and/or other sensors or clamps, generally indicated at 136, for controlling and/or monitoring fluid and/or air flow in the disposable set 102. Once again, the hematocrit sensor 135 may not be necessary if one calculates the hematocrit based on the selected parameters, as discussed above, together with the pump rate of pump 28 and the flow rate through flow path 10.

In FIG. 2, the system 100 further includes a controller, generally indicated at 138. The controller 138 may be a programmable controller that is operable to control the system 100 for various processes. An operator interface module 140 may allow for viewing of the past, current and/or upcoming operations and/or provide for operator input by way of a touch screen and/or one or more tactile controls. One or more weight scales 142, 144, 146, 148, 150 may be associated with the controller 138. In FIG. 2, such scales may be attached to a platform or stand 152 that allows one or more fluid containers to be attached to or hung from the scales and to allow for weight measurement of such containers during and/or after the processing procedure. One or more hooks 154 may also extend downwardly from a right or left side of the panel 108 to allow attachment of other fluid containers and may also be associated with a weight scale, if desired.

FIG. 3 illustrates the disposable fluid processing set 104 that may be employed for use with a fluid separation device for processing various fluids. The disposable set 104 in FIG. 3 is preferably adapted to be loaded onto a separation assembly, such as shown and disclosed in U.S. Pat. No. 5,868,696, incorporated by reference, although other separation assemblies are also possible. The set 104 in FIG. 3 shows a double needle (one for withdrawal of fluid from a patient and one for return of fluid to the patient) processing assembly although it is understood that the present disclosure is not limited to double needle processing and may include single needle and other types of processing sets.

In FIG. 3, the set 104 includes a draw needle 156 and a return needle 158, a processing chamber 160, left, middle and right pumping, flow control and valving cassettes 162, 164, 166, a first reservoir or removed red blood cell container 168, a second container or replacement red blood cell source 170, an anticoagulant source 172, a third reservoir or waste container 174, and a saline container 176. Each container 168, 170, 172, 174 and 176 may be respectively associated with a corresponding weight scale 142, 144, 146, 148, 150 for determining the amount of fluid that is removed from or added to such container. FIG. 3 also shows various tubing paths that will be discussed in further detail.

In FIG. 3, each cassette 162, 164 and 166 has a similar internal construction and, as such, only one cassette will be described and like alpha-numeric reference characters will be used for each cassette. In FIG. 3, the left cassette 162 includes at least one and preferably a plurality of pressure sensing chambers, such as PS1, PS2, PS9, and PS10, preformed fluid flow pathways and at least one and preferably a plurality of valves, such as V1, V2, V3, V4, V5, V6, V7, V8, V9, and V10, although the number and configuration of such chambers and valves are not limited to that shown and other variations are also possible including other variations for the interconnecting flow paths between such chambers and valves. Each of the chambers and valves preferably is associated with a respective portion of the respective pumping and valving station 110, 112 and 114 to control the flow of fluid.

As described above, each pump 122, 124, 126, 128, 130 and 132 may be a peristaltic pump adapted to be associated with a section of tubing to provide flow control. For example, each pump 122, 124, 126, 128, 130, and 132 may be associated with a respective tubing segment 178, 180, 182, 184, 186 and 188. Also in FIG. 3, the upper pumps 122, 124 and 126 are each associated with two pressure sensing chambers PS1 and PS2 with one being located downstream and the other located upstream of the pumps, depending on which direction is the desired flow direction, which direction may change, if desired, one or more times during and/or after the procedure. Similarly, the lower pumps 128, 130 and 132 are each associated with two pressure sensing chambers PS9 and PS10 located on either upstream or downstream side thereof. Such peristaltic pumps 122, 124, 126, 128, 130 and 132 are typically operated by rotation and include one or more outward extensions, roller or the like that act on the exterior of the respective tubing segment 178, 180, 182, 184, 186 and 188 to progressively compress or "push" fluid in the desired direction of flow.

In FIG. 3, the set 104 further includes a first flow path 190 that fluidly communicates with the draw needle 156 for withdrawing whole blood, from a patient or other blood source, such as a container of previously collected blood. An anticoagulant flow path 192 may communicate with the first flow path 190 at a Y-branch connector 194 to allow anticoagulant to mix with the withdrawn whole blood. Anticoagulant from the anticoagulant container 172 may be pumped to the first flow path 190 by the upper or anticoagulant pump 124 of the middle cassette 164 and flow through open valves V3 and V6 of such cassette to mix with the withdrawn whole blood. Also in FIG. 3, the set 104 includes a return or replacement fluid flow path 196 that fluidly communicates with the return needle 158 to allow one or more fluids, such as a replacement fluid, to flow to the patient. One or more saline flow paths 198 and 200 may also be in respective communication with the whole blood and return flow paths 190 and 196 to allow saline flow, if desired, before, during and/or after the procedure.

By way of example and not limitation, in FIG. 3, the withdrawn whole blood flows into the first flow path 190 and through the left cassette 162 preferably through open valves V7, V10 and V8 and the lower or whole blood pump 128 of such cassette. The first flow path 190 preferably communicates with the processing chamber 160 so as to allow the withdrawn whole blood from the patient to be separated into selected constituent blood components, such as red blood cells, platelets and/or plasma.

In FIG. 3, one or more outlet flow paths 202, 204, 206 and 208 may allow separated blood components, such as red blood cells, plasma and/or platelets, to separately exit the processing chamber 160. For example, separated red blood cells from the processing chamber 160 may flow through a red blood cell path 202. Separated plasma from the processing chamber 160 may flow through the plasma flow path 204. The optical detector 134, as discussed above, may be associated with the plasma flow path 204 to assist in optical detection of blood components, e.g. platelets or red cells, in the plasma constituent. The outlet flow paths 206 and 208 may allow alternative flow paths for one or more of the blood components, if desired.

In FIG. 3, separated red blood cells flowing from the processing chamber 160 preferably flow through the red blood cell flow path 202 to the red blood cell container 168. Separated red blood cells may flow through the right cassette 166 and preferably, through the open valves V8, V10 and V4 of such cassette 166 into the first container 168. If a hematocrit sensor 135 is being used, it is preferably associated with the red blood cell flow path 202 downstream of the cassette 166 to sense the hematocrit of the removed red blood cells flowing into the red blood cell container 168. Separated red blood cells preferably are pumped by operation of the lower or red blood cell pump 132 of the right cassette 166. Such red blood cell pump 132 may be employed to determine the amount of separated red blood cells removed from the patient and, accordingly, the amount of replacement fluid to be replaced to the patient. As discussed above, the removed red blood cell container 168 may also be associated with a weight scale for measuring the amount of the separated red blood cells flowing into such container during the procedure.

In FIG. 3, the separated plasma from the processing chamber 160 flows through the plasma flow path 204 for return to the patient. For example, the separated plasma may flow from the processing chamber 160 through the right cassette 166 to a first passageway 210 in communication with the return flow path 196. More particularly, the separated plasma may flow through the open valves V6 and V3 of the right cassette 166 to the plasma flow path 210. Separated plasma is preferably pumped by the upper or plasma pump 126. Separated plasma may flow into the return flow path 196 at a selected location or connector 212, which combines the plasma and replacement fluid into a combined fluid stream for return to the patient.

Also in FIG. 3, the replacement fluid flows from the replacement fluid container 170 to the patient through the return flow path 196. For example, as shown in FIG. 3, the replacement fluid flows from such container 170 through a replacement fluid source path 214 to the middle cassette 164 and through the open valves V5, V9 and V4 of such cassette. The lower or replacement pump 130 may assist the flow of the replacement fluid. In FIG. 3, the replacement fluid flows into the return flow path 196 and flows to the patient with separated plasma as a combined fluid stream. As shown in FIG. 3, the return flow path 196 may also flow through the left cassette 162, for example, through the open valves V3 and V6 of such cassette 162 as shown in FIG. 3. The combined fluid stream may also be pumped by operation of the upper left or return pump 122 to assist the return flow to the patient.

Turning to FIG. 4, another flow pattern is shown that is similar to FIG. 3 although the separated plasma preferably flows into the separated red blood cells and does not return to the patient. In particular, the separated plasma preferably flows from the processing chamber 160 into the separated red blood cells that flow into the red blood cell container 168. For example, separated plasma may flow or be pumped through the right cassette 166, for example, through the open valves V6 and V2, with the valve V3 closed to stop flow of plasma to the return flow path 196 to the patient. As a result, the separated plasma flows into the red blood cells at a selected location just downstream of the valve V2. The hematocrit sensor 135, which is preferably located at a sensing location downstream of the selected location, monitors a resulting hematocrit of the resulting plasma and red blood cell fluid stream, as described further below.

Operation of the Controller

Relative to FIGS. 1-4, the controller 24 or 138 preferably controls the addition of the separated plasma to the separated red blood cells (which also controls how much plasma is returned to the patient) so as to achieve a resulting hematocrit for the withdrawn red cells. The controller 24 or 138 preferably operates to add separated plasma into the red blood cell flow path 10 or 202 at the selected location and may communicate with a hematocrit sensor 18 or 135 preferably located downstream of the selected location of the added plasma to sense the resulting hematocrit of the separated red blood cells and plasma. If a sensor 18 or 135 is not used, then the controller could determine, via calculation, the hematocrit in flow path 10 or 202 upstream of where plasma is added to the withdrawn red blood cell flow path. The controller could then use that calculated data to further determine the amount of plasma that is needed to add to the red blood cells to achieve the desired hematocrit.

A hematocrit sensor could also be located upstream of the location where plasma is added to the withdrawn red cell flow path. In that case, the sensor would sense the hematocrit of the withdrawn red cells and the controller could use that data to calculate the amount of plasma that is needed to add to the red cells to achieve the desired hematocrit (e.g., substantially equal to the known hematocrit of the replacement red cells) and control a plasma pump or valve to direct that amount of plasma into the withdrawn red cell flow path.

In FIGS. 1-4, the controller 24 or 138 may achieve a desired resulting hematocrit by alternating the separated plasma flow between addition into the red blood cells and return flow to the patient one or more times. By way of example, the controller 24 or 138 may control the addition of separated plasma into the red blood cells by opening the valves 28 or V2 and closing the valves 26 or V3 to allow such addition of plasma. Such addition of plasma typically will lower the resulting hematocrit that is sensed by the hematocrit sensor 18 or 135. In FIGS. 1 and 3, the controller 24 or 138 may also control the separated plasma to flow to the patient through the branch 12 or the passageway 210 and to not flow into the separated red blood cells. For example, the controller 24 or 138 may control the flow of separated plasma to the patient through the open valves 26 or V3 and while the valves 28 or V2 are closed. Such flow of plasma to the patient will typically raise the resulting hematocrit of the separated red blood cells, depending on the donor hematocrit, flow rate and separation speed of the separator 6 or 160. The controller 24 or 138 preferably alternates between flow of separated plasma to the patient and flow into the red blood cells as needed to adjust the resulting hematocrit of the withdrawn red cells to achieve the desired resulting hematocrit in the first container 16 or 168. The controller 24 or 138 may be programmed with the desired hematocrit and/or the controller 24 or 138 may allow for operator input that selects the desired hematocrit, such as a hematocrit substantially equal to the known hematocrit of the replacement red cells. Although, as described above, the plasma flow may be alternated, as needed based on the resulting hematocrit that is sensed by the hematocrit sensor 18 or 135, it is also possible that the controller may alternate flow of plasma based on a specific time interval to achieve a desired resulting hematocrit or employ a proportional flow control valve that allows a continuous selected flow rate of plasma to the withdrawn red cell flow path.

In one example, the controller 24 or 138 may control the resulting hematocrit so as to achieve a desired hematocrit or a hematocrit within a desired range of about 60%-65%. For example, the controller 24 or 138 preferably controls the flow of plasma, such as by alternating the flow of separated plasma between flow to the patient and flow to the red blood cells, such that the added plasma into the red blood cells achieves a desired resulting hematocrit within the range of about 60%-65%.

In another aspect, the controller 24 or 138 may be operated to achieve a resulting hematocrit that is substantially the same as a known hematocrit of the replacement red blood cells. For example, if the known hematocrit of the replacement red blood cells is about 60%, then the controller 24 or 138 may allow the addition of separated plasma to the red blood cells so as to achieve a resulting hematocrit of about 60%. Other known hematocrit valves are also possible and not limited to the above described valve.

In a further aspect, a method for controlling hematocrit during a blood processing procedure may be employed with any of the above described embodiments. The method may include withdrawing whole blood from a patient and separating the whole blood withdrawn from the patient into at least separated plasma and separated red blood cells having a hematocrit. The method may also include sensing the hematocrit of the separated red blood cells (either before or after addition of separated plasma), such as by use of a hematocrit sensor 18 or 135, and further include adding separated plasma to separated red blood cells as necessary to achieve a desired resulting hematocrit. The method may be particularly useful to control the resulting hematocrit at about a desired level, such as for example, at about a level that is substantially the same and preferably the same as a known hematocrit of the replacement red blood cells that flow into the patient. The method may further include alternately returning separated plasma to the patient and adding separated plasma to the separated red blood cells.

In a yet further aspect, a method for controlling hematocrit during a blood processing procedure may include introducing replacement red blood cells of known hematocrit into a patient. The method also may include withdrawing whole blood from the patient and separating the whole blood withdrawn from the patient into at least separated plasma and separated red blood cells having a hematocrit. The method may further include sensing the hematocrit of the red blood cells, such as with the use of the hematocrit sensor 18 or 135, and adding separated plasma to separated red blood cells as necessary to achieve a desired resulting hematocrit that is substantially the same as the known hematocrit of the replacement red blood cells. As described above, the method may include alternately returning separated plasma to the patient and adding separated plasma to the separated red blood cells.

As can be seen from the above description, the present disclosure has several different aspects, which are not limited to the specific structures shown in the attached drawings. Variations of these concepts or structures may be embodied in other structures for carrying out other applications in the medical or other fields without departing from the present invention as set forth in the appended claims.

What is claimed is:

1. A system for controlling hematocrit during a blood processing procedure including:
   a first flow path for flowing whole blood from a patient;
   a separator communicating with the first flow path for separating at least red blood cells from plasma;
   a second flow path communicating with the separator for flowing the separated plasma from the separator;
   a third flow path communicating with the separator for flowing the separated red blood cells from the separator;
   a replacement red blood cell flow path communicating directly or indirectly with a patient configured to flow replacement red blood cells of a known hematocrit from a third party source thereof;
   a flow controller associated with the second and third flow paths to control fluid communication between the second and third flow paths and to control addition of separated plasma to the separated red blood cells; the resulting red blood cells and plasma having a resulting hematocrit; and the flow controller calculating the hematocrit in the third flow path or communicating with a hematocrit sensor operatively associated with the third flow path either upstream or downstream of the communication between the second and third flow paths, the flow controller controlling the amount of separated plasma added to the third flow path and thus controlling the resulting hematocrit based on the calculated hematocrit or the output of the hematocrit sensor.

2. The system of claim 1 wherein the flow controller is programmable and is programmed to control the resulting hematocrit at about a desired level.

3. The system of claim 1 wherein the resulting hematocrit is selectable to be substantially the same as the known hematocrit of the replacement red blood cells.

4. The system of claim 1 wherein the second flow path is adapted to communicate directly or indirectly with the patient to allow separated plasma to return to the patient when such separated plasma is not added to the separated red blood cells in the third flow path.

5. The system of claim 4 wherein the controller is adapted to alternate the flow of separated plasma between flow to the third flow path and return flow to the patient.

6. The system of claim 1 wherein the hematocrit sensor senses the hematocrit in the third flow path at least either upstream or downstream of the addition of separated plasma.

7. A system for controlling hematocrit during a blood processing procedure including:
a replacement fluid flow path configured to communicate with replacement red blood cells from a third party source of replacement red blood cells having a known hematocrit;
a first flow path for flowing whole blood from a patient;
a separator for separating the whole blood to separate at least red blood cells from plasma;
a second flow path communicating with the separator for flowing the separated plasma from the separator;
a third flow path communicating with the separator for flowing the separated red blood cells from the separator;
a controller associated with the second and third flow paths to control fluid communication between the second and third flow paths so as to control addition of separated plasma to the separated red blood cells, the resulting red blood cells and plasma having a resulting hematocrit; and
the flow controller calculating the hematocrit in the third flow path or communicating with a hematocrit sensor operatively associated with the third flow path to determine the hematocrit therein, the flow controller controlling the amount of separated plasma added to the third flow path and thus controlling the resulting hematocrit based on the calculated hematocrit or the output of the hematocrit sensor.

8. The system of claim 7 wherein the second flow path is adapted to communicate directly or indirectly with the patient to allow separated plasma to return to the patient when such separated plasma is not added to the separated red blood cells in the third flow path.

9. The system of claim 7 wherein the controller is adapted to alternate the flow of separated plasma between flow to the third flow path and return flow to the patient.

10. The system of claim 7 wherein the controller is programmable and is programmed to control the resulting hematocrit at about a desired level that is substantially the same as the known hematocrit.

11. A method for controlling hematocrit of withdrawn blood during a therapeutic red blood cell exchange procedure in which replacement red blood cells of a known hematocrit originating from a third party donor are transfused into a patient including:
withdrawing whole blood from the patient;
introducing the replacement red blood cells of a known hematocrit into the patient;
separating the whole blood withdrawn from the patient into at least separated plasma and separated red blood cells having a hematocrit;
determining the hematocrit of the separated red blood cells; and
adding separated plasma to the separated red blood cells as necessary to achieve a desired resulting hematocrit wherein the resulting hematocrit is substantially the same as the known hematocrit of the replacement red blood cells; and
returning any remaining separated plasma to the patient.

12. The method of claim 11 including controlling the resulting hematocrit at about a desired level.

13. The method of claim 11 further including alternately returning separated plasma to the patient and adding separated plasma to the separated red blood cells.

14. The method of claim 11 wherein determining the hematocrit further comprises sensing the hematocrit upstream of the addition of separated plasma.

15. The method of claim 11 wherein determining the hematocrit further comprises sensing the hematocrit downstream of the addition of separated plasma.

16. The method of claim 11 wherein determining the hematocrit further comprises calculating the hematocrit at a location upstream or downstream of the addition of separated plasma.

* * * * *